US006770262B2

(12) United States Patent
Lehman et al.

(10) Patent No.: US 6,770,262 B2
(45) Date of Patent: Aug. 3, 2004

(54) NASAL ADMINISTRATION OF AGENTS FOR THE TREATMENT OF GASTROPARESIS

(75) Inventors: Laura S. Lehman, Palo Alto, CA (US); David Tierney, Shrewsbury, NJ (US); Anastassios D. Retzios, San Ramon, CA (US); Michael Petrone, Voorhees, NJ (US); David Young, Ellicott City, MD (US); Carol B. Trapnell, Ellicott City, MD (US); Ruth Oliver, Maidenhead (GB)

(73) Assignee: Questcor Pharmaceuticals, Inc., Union City, CA (US)

( * ) Notice: Subject to any disclaimer, the term of this patent is extended or adjusted under 35 U.S.C. 154(b) by 0 days.

(21) Appl. No.: 09/821,139

(22) Filed: Mar. 29, 2001

(65) Prior Publication Data

US 2002/0065321 A1 May 30, 2002

Related U.S. Application Data

(60) Provisional application No. 60/193,181, filed on Mar. 30, 2000.

(51) Int. Cl.$^7$ .......................... A61K 9/12; A61K 31/165
(52) U.S. Cl. ........................... 424/45; 424/43; 424/400; 514/619; 514/397; 514/471; 128/200.14
(58) Field of Search ........................... 424/45, 43, 400; 514/619, 397, 471; 128/200.14

(56) References Cited

U.S. PATENT DOCUMENTS

| | | | |
|---|---|---|---|
| 4,624,965 A | 11/1986 | Wenig | |
| 4,729,997 A | 3/1988 | Wenig | |
| 5,116,857 A | 5/1992 | Acher | |
| 5,576,317 A | 11/1996 | Gonsalves | |
| 5,578,632 A | * 11/1996 | Tyers | .......................... 514/397 |
| 5,760,086 A | 6/1998 | Psilogenis | |

FOREIGN PATENT DOCUMENTS

HU 210115 B 2/1995

OTHER PUBLICATIONS

Robins, product information on Rglan®, obtained from on–line PDR.*
Bateman, et al., 1980 "The Pharmacokinetics Of Metoclopramide In Man With Observations In The Dog," Br. J. Clin. Pharmac. 9:371–377.
Chiara, et al., 1995 "Prevention of Delayed Emesis with Metoclopramide and Dexamethasone in Patients Receiving Moderately Emetogenic Cytotoxic Treatment," Anticancer Research 15:1597–1599.
Clark, et al., 1986, "Antiemetic (AE) trials to control delayed vomiting (V) following high–dose cisplatin (DDP)", Proceedings of ASCO 5:257, abstr. 1005.
Clark, et al., 1993 "Delayed emesis: A dilemma in anti-emetic control", Support Care Cancer 1:182–185.

Cubeddu, et al., 1993, "Participation of serotonin on early and delayed emesis induced by initial and subsequent cycles of cisplatinum–based chemotherapy: Effects of antiemetics", J. Clin. Pharmacol. 33:691–697.
De Mulder, et al., 1990, "Ondansetron compared with high–dose metoclopramide in prophylaxis of acute and delayed cisplatin–induced nausea and vomiting", Ann. of Internal Med. 113:834–840.
Du Bois, et al., 1995, "Cisplatin–induced alterations of serotonin metabolism in patients with or without emesis following chemotherapy", Oncol. Rep. 2:839–842.
Gandara, 1991, "Progress in the control of acute and delayed emesis induced by cisplatin", Eur. J. Cancer 27:S9–S11.
Gandara, et al., 1992, "The delayed–emesis syndrome from cisplatin: Phase III evaluation of ondansetron versus placebo", Semin. Oncol. 19:67–71.
Gralla, et al., "Management of Chemotherapy–induced Nausea and Vomiting" http://www.cancernetwork.com/home/nausea.htm Last viewed Oct. 11, 2002.
Gralla, et al., 1987, "The management of Chemotherapy–induced Nausea and Vomiting", Medical Clinics of North America (Cancer Pain) 71:289–301.
Grunberg, et al., 1988, "Oral metoclopramide with or without diphenhydramine: Potential for prevention of late nausea and vomiting induced by cisplatin", J. of the Natl. Cancer Inst. 80:864–868.
Jones, et al., 1991, "Comparison of dexamethasone and ondansetron in the prophylaxis of emesis induced by moderately emetogenic chemotherapy", Lancet 338:483–486.
Kris et al., 1989, "Controlling delayed vomiting: Double–blind, randomized trial comparing placebo, dexamethasone alone, and metoclopramide plus dexamethasone in patients receiving cisplatin", J. of Clin. Oncol. 7:108–114.
Kris, et al., 1992, "Oral ondansetron for the control of delayed emesis after cisplatin", Cancer Suppl. 70:1012–1016.
Lee, et al., 1994, "Ondansetron compared with ondansetron plus metoclopramide in the prevention of cisplatin–induced emesis", J. of Korean Med. Sci. 9:369–375.
Levitt, et al., 1993, "Ondansetron compared with dexamethasone and metoclopramide as antiemetics in the chemotherapy of breast cancer with cyclophosphamide, methotrexate, and fluorouracil", New England J. of Med. 328:1081–1084.
Li, et al., 1991, "Control of cisplatin–induced delayed emesis", Chin. Med. J. (Taipei) 48:451–455. (With English abstract).

(List continued on next page.)

Primary Examiner—Michael G. Hartley
Assistant Examiner—Mina Haghighatian
(74) Attorney, Agent, or Firm—Jones Day

(57) ABSTRACT

The present invention is directed to a method for the treatment of gastroparesis by the use of metoclopramide nasal formulation.

35 Claims, 10 Drawing Sheets

OTHER PUBLICATIONS

Figure 1:
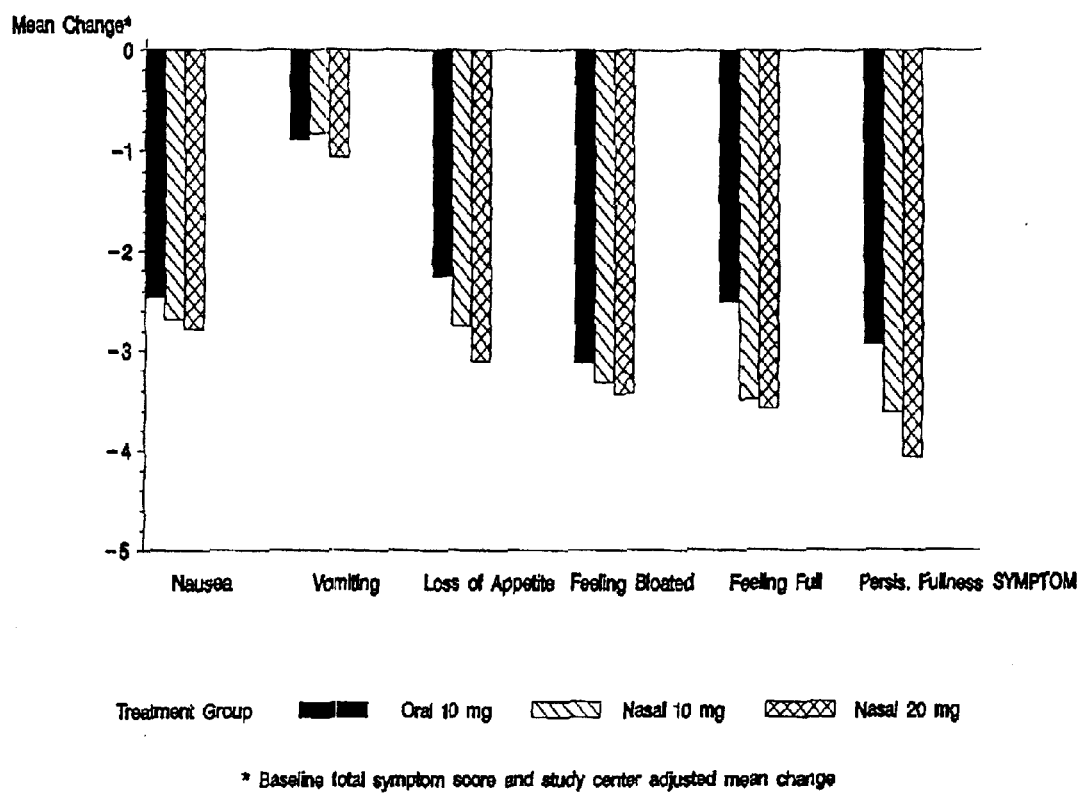

Locatelli, et al., 1995 "Tolerability and Safety of Nasally Administered Metoclopramide (MCP) for the Prevention of CIS–Platinum (CDDP) Induced Delayed Emesis", Proceedings of ASCO vol. 14 Mar. 1995, abstr. 1759.

Madej, et al., 1994, "A report comparing the use of tropisetron (Navoban), a 5–HT$_3$ antagonist, with a standard antiemetic regimen of dexamethasone and metoclopramide in cisplatin–treated patients under conditions of severe emesis", *Semin. Oncol.* 21:3–6.

Medical Economics Co., 1999, PDR 53th Edition 1999, "Physicians's Desk Reference" 2643–2545.

Medical Economics Co., 2000, PDR 54th Edition 2000, "Physician's Desk Reference" 2603–2605.

Moreno, et al., 1992, "Comparison of three protracted antiemetic regimens for the control of delayed emesis in cisplatin–treated patients", *Eur. J. Cancer* 28:1344–1347.

Navari, et al., 1995, "Oral ondansetron for the control of cisplatin–induced delayed emesis: A large, multicenter, double–blind, randomized comparative trial of ondansetron versus placebo", *J. of Clin. Oncol.* 13:2408–2416.

Nino, et al., 1987, "A randommized controlled trial of acute and delayed cisplatin–induced emesis with metoclopramide, dexamethasone and prochlorperazine", *Jpn. J. Cancer Chemother.* 14:2881–2884. (With English summary).

O'Brien, et al., 1989, "The role of metaclopramide in acute and delayed chemotherapy induced emesis: A randomized double blind trial", *Br. J. Cancer* 60:759–763.

Ogawa, 1982, "Metoclopramide as an antiemetic in chemotherapy", *New England J. of Med. Correspond.* 307:249–250.

Roila, et al., 1994 "Cisplatin–induced delayed emesis: Pattern and prognostic factors during three subsequent cycles," Annals of Oncology 5:585–589.

Roila, et al., 1991, "Predictive factors of delayed emesis in cisplatin–treated patients and antiemetic activity and tolerability of metoclopramide or dexamethasone", *Am. J. Clin. Oncol. (CCT)* 14:238–242.

Scaglione, et al., 1993, "Pharmacokinetics and bioavailability of metoclopramide nasal spray versus metoclopramide intravenous in healthy volulnteers and cancer patients", *Arzneim.–Forsch/Drug. Res.* 43:986–988.

Shinkai, et al., 1989 "Control of Cisplatin–induced Delayed Emesis with Metoclopramide and Dexamethasone: a Randomized Controlled Trial," Jpn. J. Clin. Oncol. 19:40–44.

Soukop, et al., 1992, "Ondansetron compared with metoclopramide in the control of emesis and quality of life during repeated chemotherapy for breast cancer", *Oncol. .* 49:295–304.

Strum, et al., 1985, "Management of cisplatin (DDP)–induced delayed–onset nausea(N) and vomiting(V): Preliminary results with 2 drug regimens", *Proceedings of ASCO* 4:263, abstr. C–1024.

Taylor, et al., 1986 "Oral Bioavailability of High–Dose Metoclopramide," Eur. J. Clin. Pharmacol. 31:41–44.

Tomirotti, et al., 1994 "Efficacy and tolerability of nasally administered compared to parenterally administered metoclopramide in the symptomatic treatment of chemotherapy–induced emesis in cancer outpatients," Support Care Cancer 2:389–392.

Vogt, et al., 1993 "Oral Medium–Dosed Metoclopramide versus Placebo as Highy Effective Antiemetic Prophylaxis in In– and Outpatients on Noncisplatin Chemotherapy," Oncology 50:81–85.

Marketing Authorization for Pramidin in Italy, dated Nov. 18, 1997—Ministerial Decree No. 495/97 with English translation; published in Official Gazette on Dec. 20, 1997.

Crinos Industria Pharmacobiologica S.p.A.—package inserts for Pramidin 10 and Pramidin 20 with English translation, Apr. 1999.

Drenth and Engels, 1992, "Diabetic gastroparesis. A critical reappraisal of new treatment strategies", Drugs 44:537–553.

Longo et al., 1993, "Prokinetic agents for lower gastrointestinal motility disorder", , Dis. Colon Rectum 36:696–708.

Perkel et al., 1980, "Metoclopramide therapy in fifty–five patients with delayed gastric emptying", Am. J. Gastroenterol. 74:231–236.

Ormrod and Goa, "Intranasal Metoclopramide" Reprinted from *Drugs* 58(2):315–324 (Aug. 1999).

* cited by examiner

NASAL ADMINISTRATION OF AGENTS FOR THE TREATMENT OF GASTROPARESIS

This application claims priority to provisional application serial No. 60/193,181, filed on Mar. 30, 2000, which is incorporated herein by reference in its entirety.

1. FIELD OF THE INVENTION

The present invention is directed to a method for treating gastroparesis. More particularly, the present invention is directed to a method for treating gastroparesis typically caused by diabetes mellitus (including type 1 and type 2 diabetes), postviral syndromes, anorexia nervosa, malnutrition, alcoholism, surgery on the stomach or vagus nerve, medications, particularly anticholinergics and narcotics which slow contractions in the intestine, gastroesophageal reflux disease, smooth muscle disorders such as amyloidosis and scleroderma, nervous system diseases (including abdominal migraine and Parkinson's disease), or metabolic disorders (including hypothyroidism) with the nasal administration of metoclopramide.

2. BACKGROUND OF THE INVENTION

The vagus nerve controls the movement of food through the digestive tract. Normally, stomach muscles contract about three times a minute and the stomach empties within 90–120 minutes after eating. When the vagus nerve is damaged or dysfunctional, stomach muscles do not work properly and the stomach contraction becomes sluggish and/or less frequent. As a result, the movement of food is slowed or stopped. Gastroparesis is the medical term for this condition.

Typical symptoms of gastroparesis are nausea, vomiting, early satiety, weight loss, abdominal bloating, abdominal discomfort, epigastric pain, anorexia. These symptoms may be mild or severe. In addition, since food lingers too long in the stomach, gastroparesis can lead to complications such as bacterial overgrowth from the fermentation of food, hardening of food into solid masses which are called bezoars that may cause nausea, vomiting, and obstruction in the stomach. Bezoars can be dangerous if they block the passage of food into the small intestine.

Major causes of gastroparesis include diabetes, postviral syndromes, anorexia nervosa, surgery on the stomach or vagus nerve, medications, particularly anticholinergics and narcotics (drugs that slow contractions in the intestine), gastroesophageal reflux diseases, smooth muscle disorders such as amyloidosis and scleroderma, nervous system diseases such as abdominal migraine and Parkinson's disease, and metabolic disorders such as hypothyroidism.

As stated above, diabetes is a major cause of gastroparesis. Blood glucose levels of diabetic patients often remain high over a long period of time. High blood glucose causes chemical changes in nerves and damages the blood vessels that carry oxygen and nutrients to the magus nerves. As a result, at least 20 percent of people with type 1 diabetes develop gastroparesis. Gastroparesis also occurs in people with type 2 diabetes, although less often.

Metoclopramide in oral and injectable forms, cisapride, erythromycin, and domperidone have been investigated for the treatment of gastroparesis. Metoclopramide (MCP) stimulates stomach muscle contractions to help empty food. It also helps reduce nausea and vomiting. Metoclopramide is taken 20 to 30 minutes before meals and at bedtime. Traditionally, treatment of gastroparesis is via injection or oral route. Metoclopramide is currently available in a tablet form, injection form, and syrup form under the name Reglan® (A.H. Robbins Company). The injection form has an onset of action of about 1–3 minutes after intravenous administration and an onset of action of about 10–15 minutes after intramuscular administration. However, injections, particularly daily multiple injections, are often very painful and inconvenient. Intravenous administration often requires a hospital setting. As a result, compliance (compliance= following dosage regimen prescribed) is often very poor. Metoclopramide in the tablet or syrup form can be effectively and rapidly absorbed through the GI tract by healthy persons. Pharmacokinetics studies of subjects show that oral bioavailability of metoclopramide is approximately 80%±15.5%. Peak plasma concentrations occur at about 1–2 hours after a single oral dose. However, for patients with gastroparesis, metoclopramide absorption through the GI tract is unpredictable and far less effective, with predictability and effectiveness having an inverse relationship to the severity of the symptom, i.e., the more severe the symptoms, the less likely that oral administration is an option. Further complicating the matter of oral administration of metoclopramide is the fact that patients with gastroparesis often have symptoms such as vomiting and nausea. If vomiting takes place, the amount of metoclopramide that remains in the stomach is unknown, and the result of treatment is even less predictable.

Side effects of metoclopramide include fatigue, sleepiness, depression, anxiety, and difficulty with physical movement. Mental depression has occurred in patients with and without prior history of depression. Symptoms range from mild to severe, including suicidal ideation and suicide. Other symptoms such as involuntary movements of limbs and facial grimacing, torticollis, oculogyric crisis, rhythmic protrusion of tongue, bulbar type of speech, trismus, and dystonic reactions such as stridor and dyspnea.

These side effects may interfere with patient compliance with the drug regimen prescribed, as well as interfere with the patient's ability to effectively communicate the nature and severity of this and other side effects. Poor compliance or non-compliance is observed in about 25% of patients with an oral medication regimen. Due to nausea and vomiting associated with gastroparesis, patients are even more reluctant to comply with the oral regimen.

U.S. Pat. No. 4,624,965 (hereinafter Wenig) discusses nasal administration of MCP. No experience with human subjects using a nasal spray formulation of MCP (MCP ns) is disclosed within Wenig. Furthermore, Wenig did not disclose using any forms of MCP, or any particular regimen for the purpose of treating gastroparesis.

U.S. Pat. No. 5,760,086 to Psilogenis (hereinafter Psilogenis) is solely directed to nasal administration of MCP for the treatment of a specific disease state known as delayed onset emesis, particularly emesis induced by chemotherapy. Psilogenis did not disclose nasal administration of MCP for the purpose of treating gastroparesis.

In view of the above, there is a clear need for an improved method of treating gastroparesis. Specifically, there is a need to develop an improved method of administering metoclopramide. More specifically, there is a need to develop an improved method of administering metoclopramide safely, effectively, and consistently.

3. SUMMARY OF THE INVENTION

The present invention is directed to providing a method for treating gastroparesis by using a dosage form of MCP that avoids or reduces the incidence of patient non-compliance. Another object of the present invention is to provide a method for treating gastroparesis by nasally administering MCP which avoids or reduces the incidence of side-effects experienced by patients.

Yet another Object of the present invention is to provide a method for treating gastroparesis caused by diabetes by using a dosage form of MCP that avoids or reduces the problem of patient non-compliance.

It is still another object of the present invention to provide a method for treating gastroparesis caused by type 1 or type 2 diabetes by using a dosage form of MCP that avoids or reduces the problem of patient non-compliance.

It is yet still another object of the present invention to provide a method for sufficiently treating gastroparesis caused by diabetes using a dosage form of MCP that avoids or reduces the incidence of side-effects experienced by patients.

It is even yet still another object of the present invention to provide a method for sufficiently treating gastroparesis caused by type 1 or type 2 diabetes using MCP nasal spray that avoids or reduces the severity of side-effects experienced by patients.

It is further an object of the present invention to provide a method for sufficiently controlling gastroparesis caused by diabetes by nasally administering MCP that avoids or reduces the problems associated with patient non-compliance.

These and other objectives of the present invention are accomplished by administering intranasally to patients suffering from gastroparesis a therapeutically effective dosage of MCP in a pharmaceutically acceptable dosage form which is therapeutically and medically acceptable.

4. BRIEF DESCRIPTION OF THE DRAWINGS

Figure 2A:
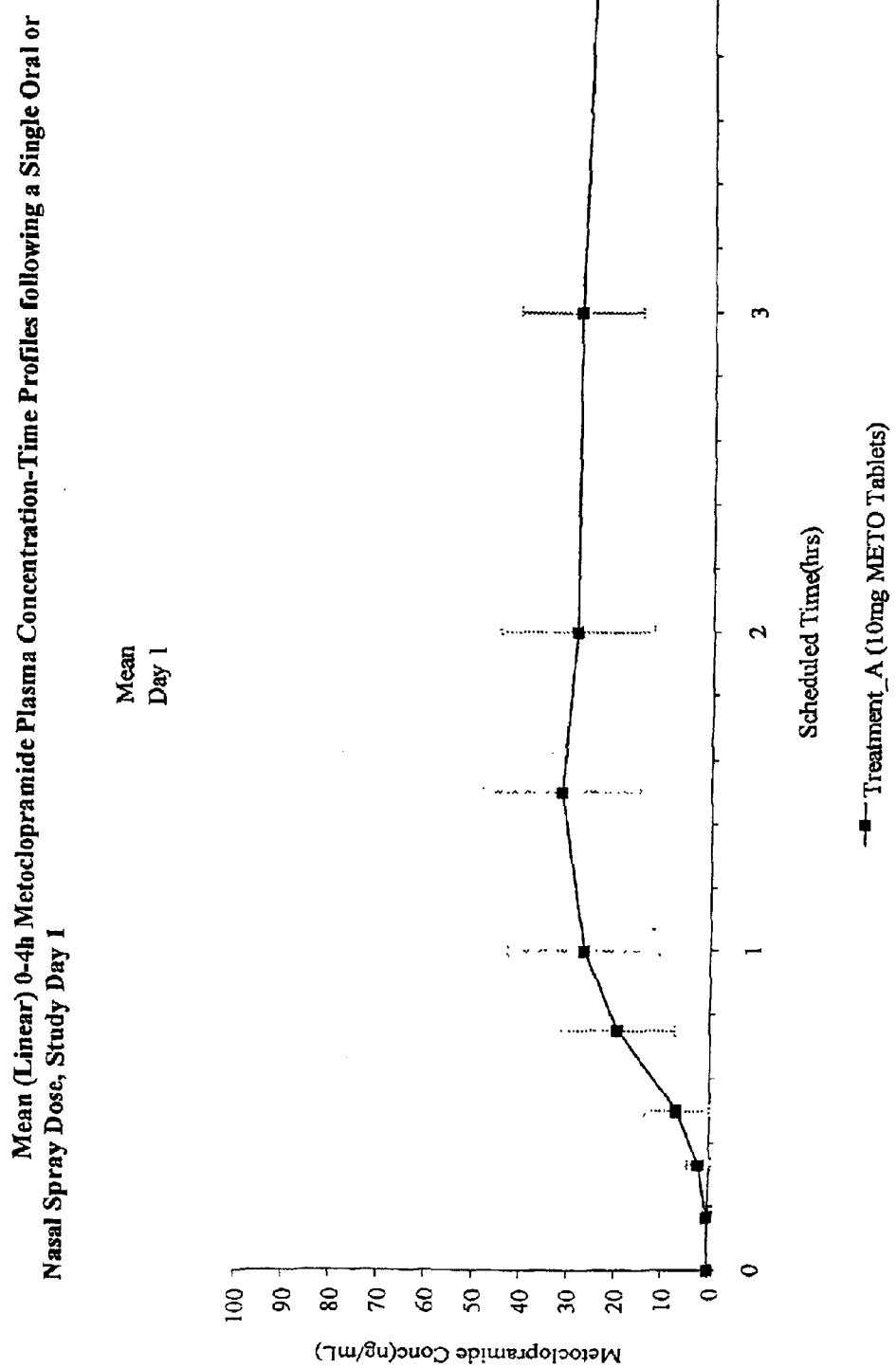
Figure 2B:
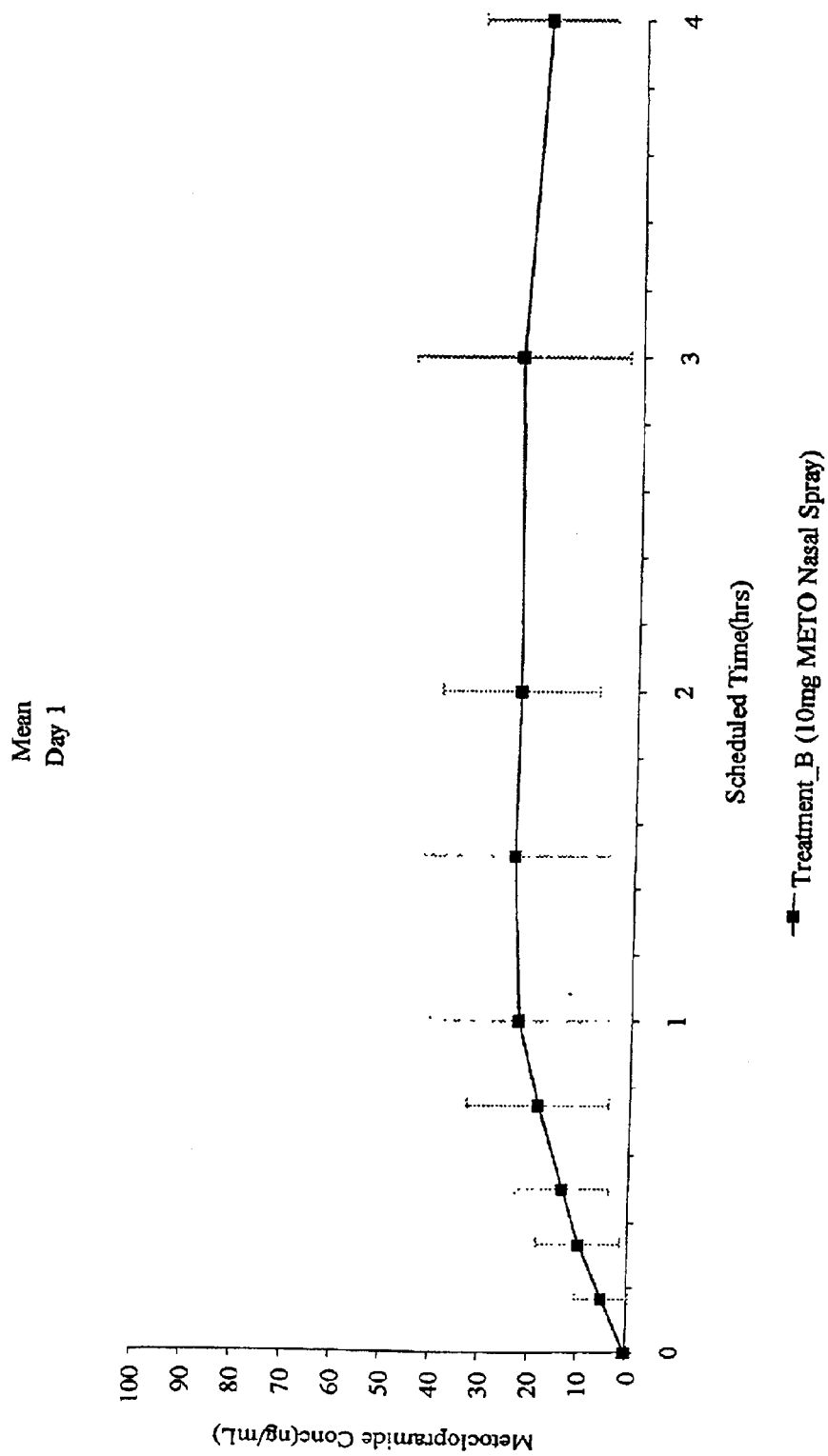
Figure 2C:
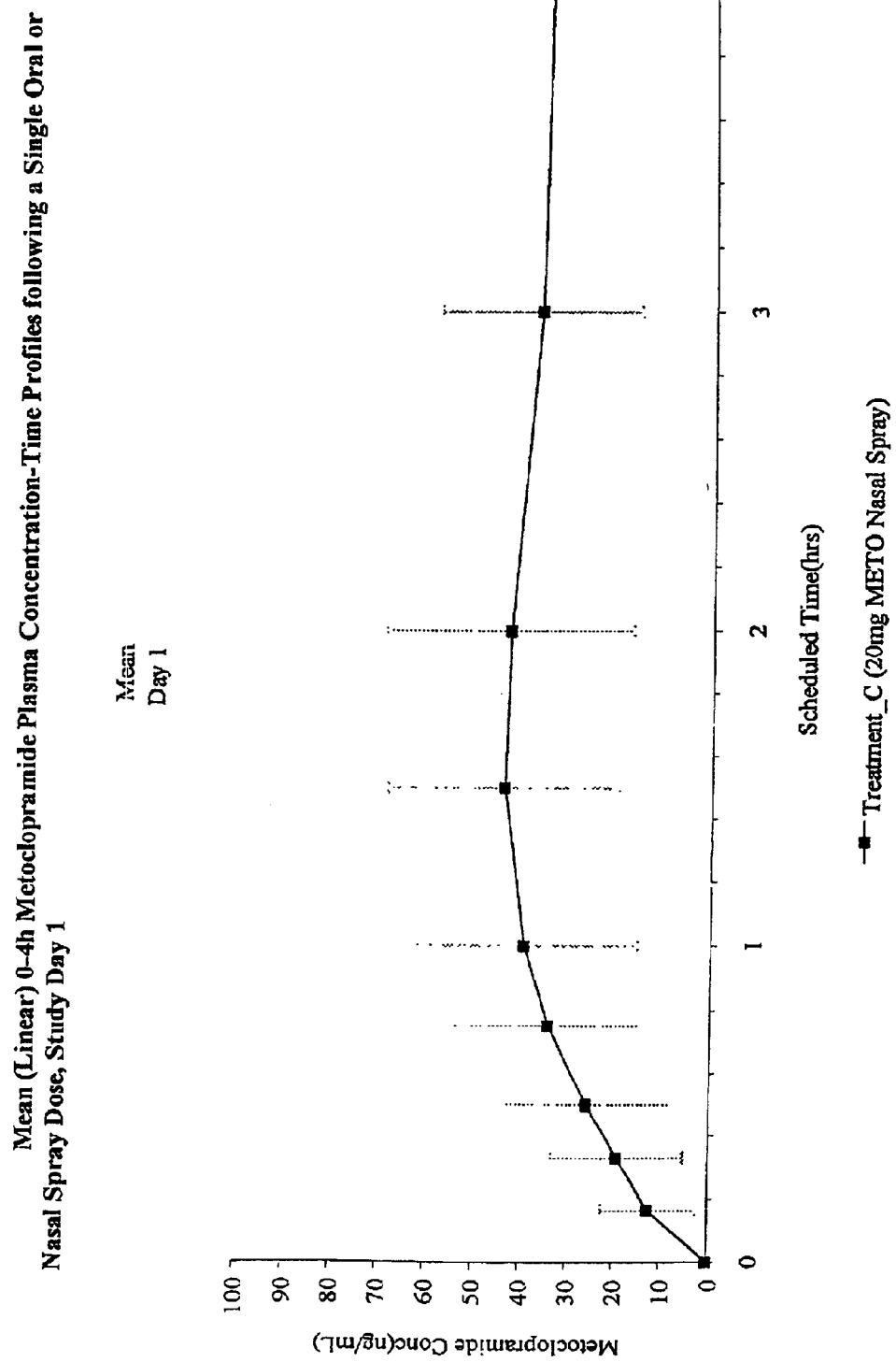
Figure 3A:
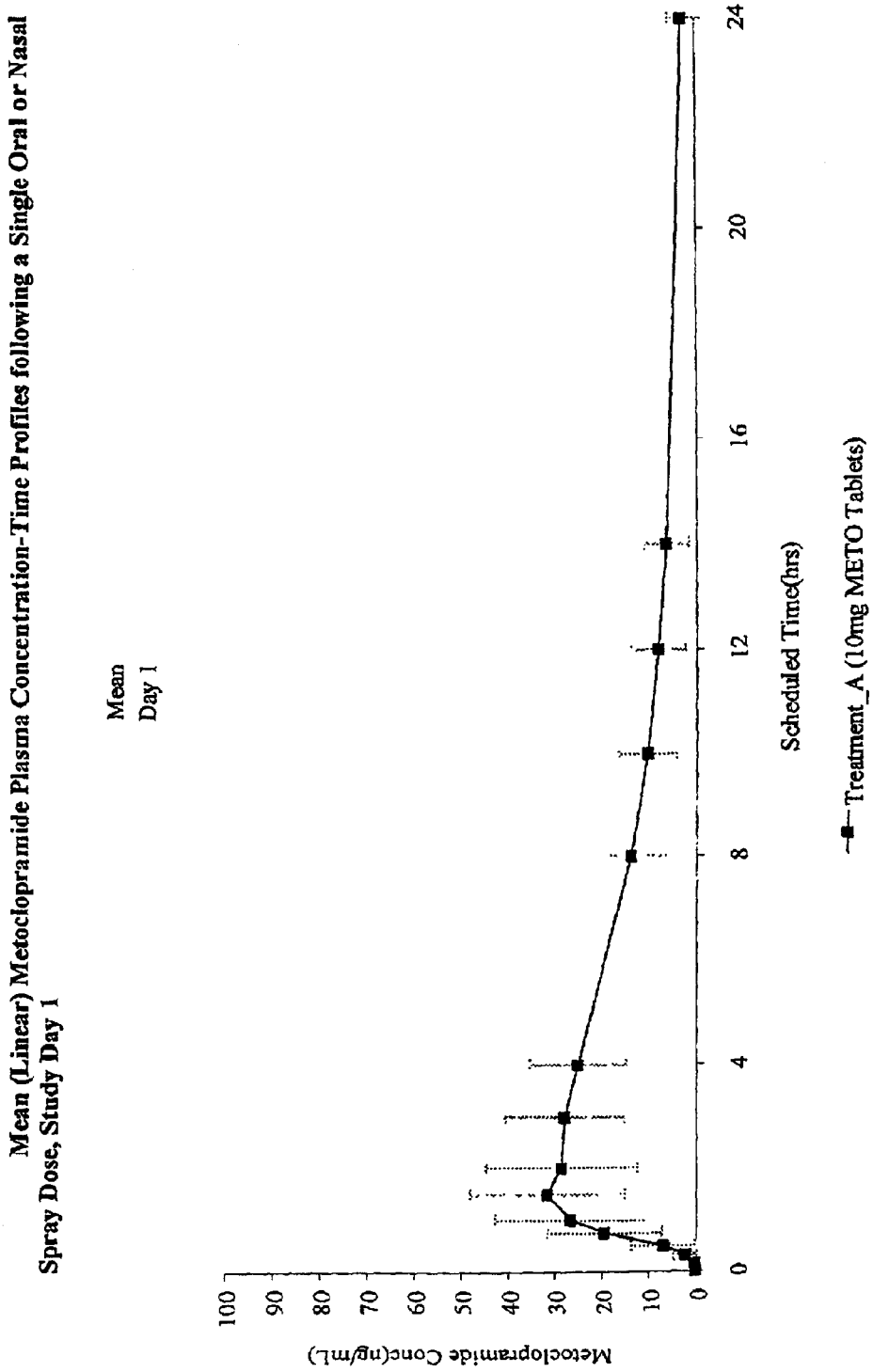
Figure 3B:
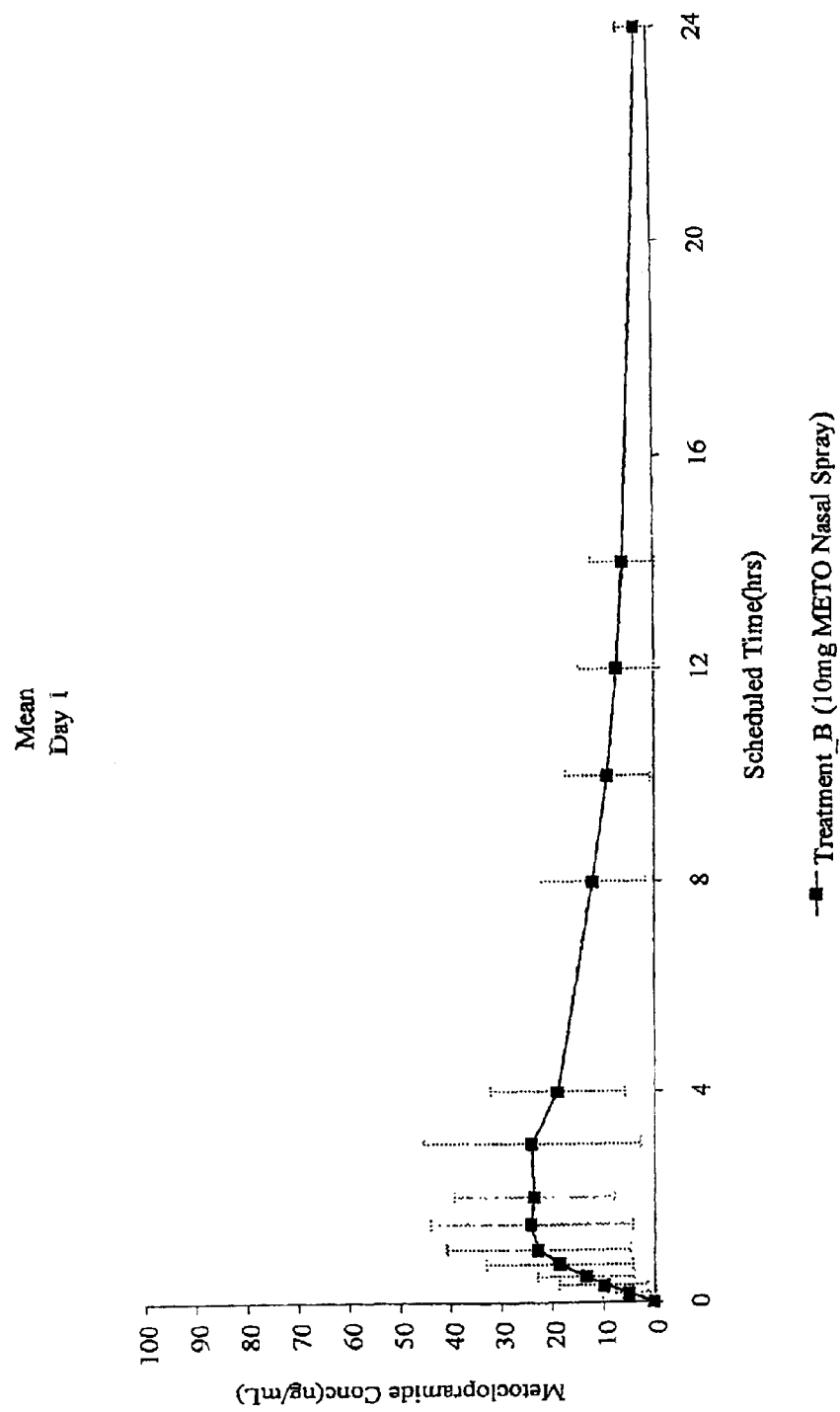
Figure 3C:
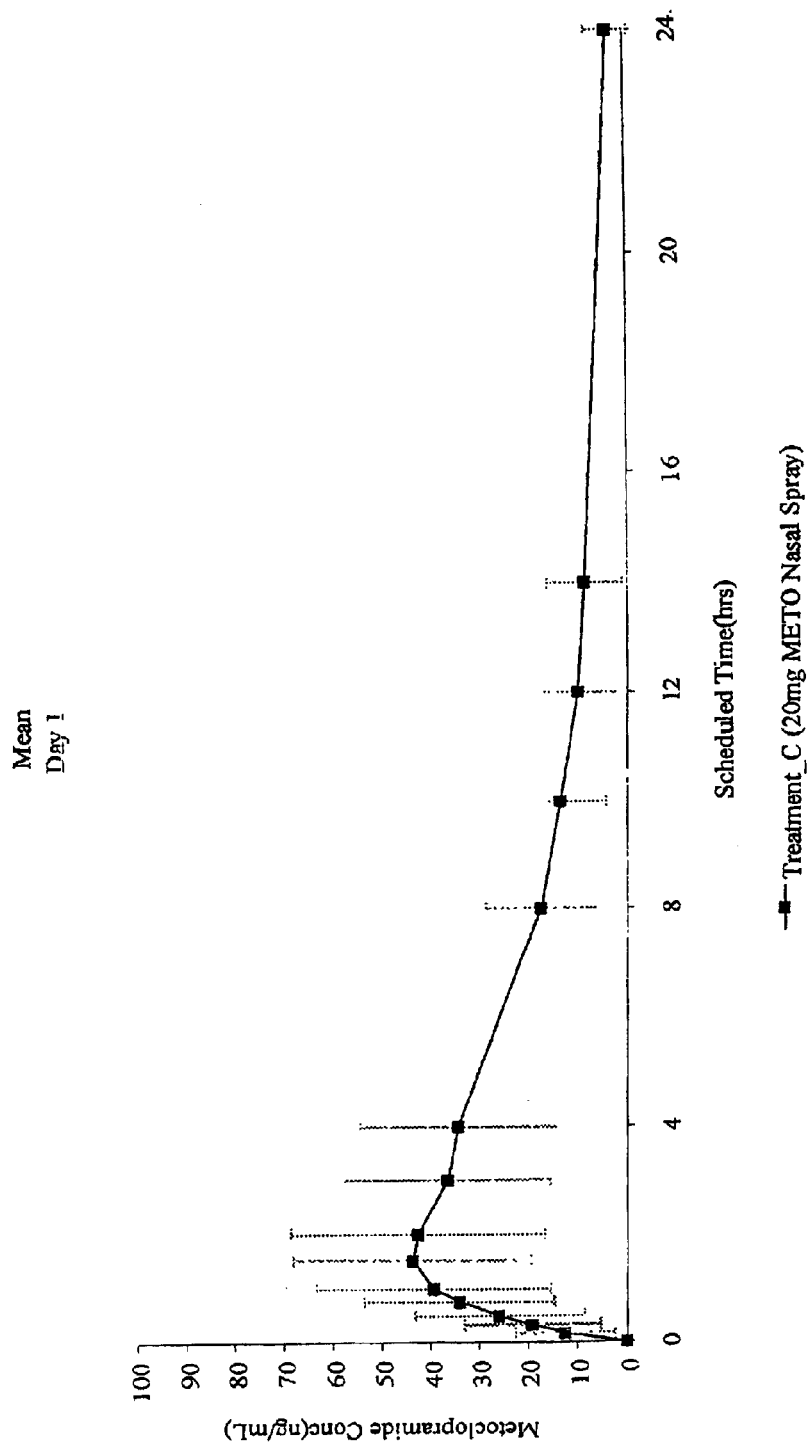
Figure 4A:
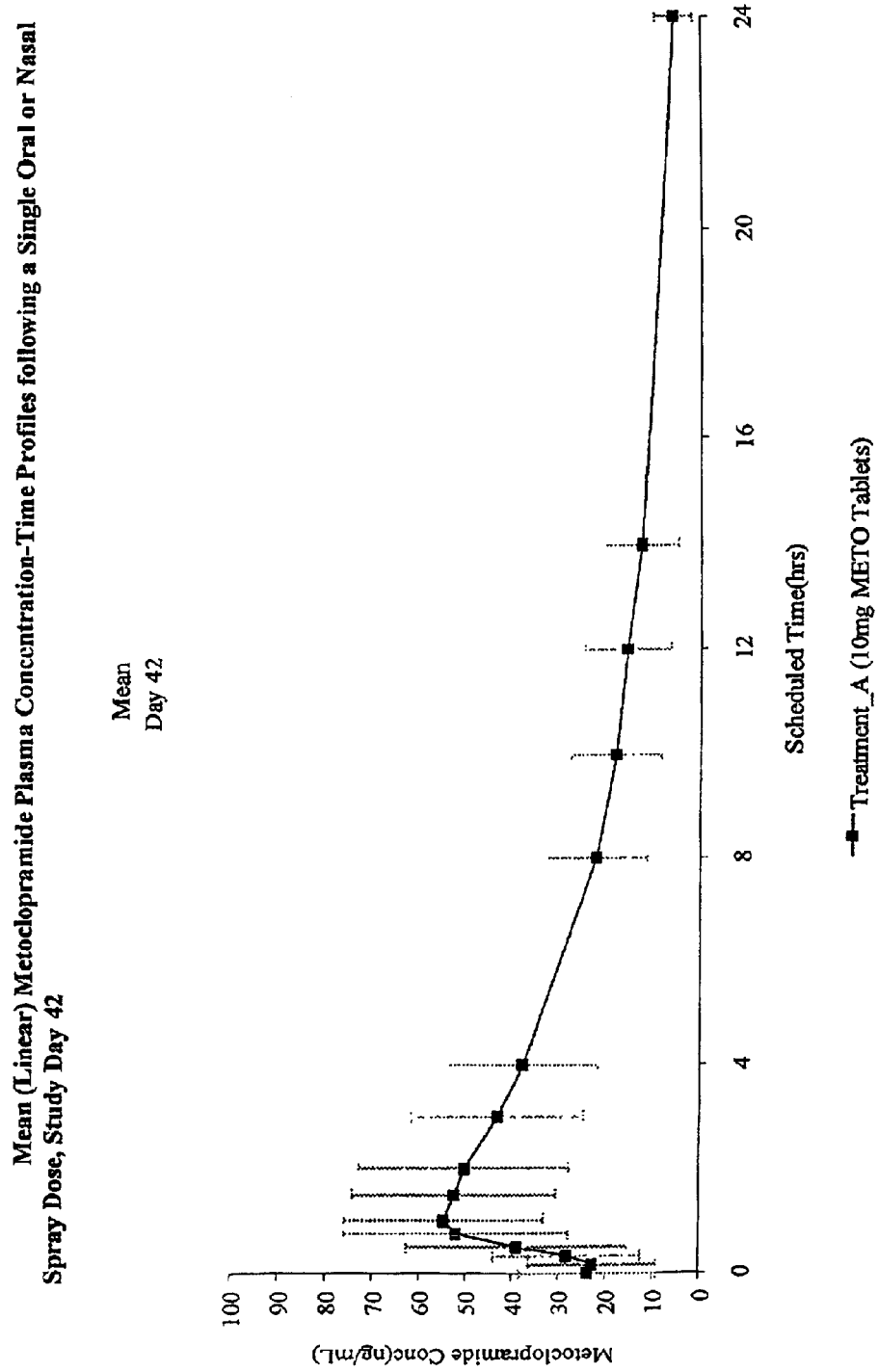
Figure 4B:
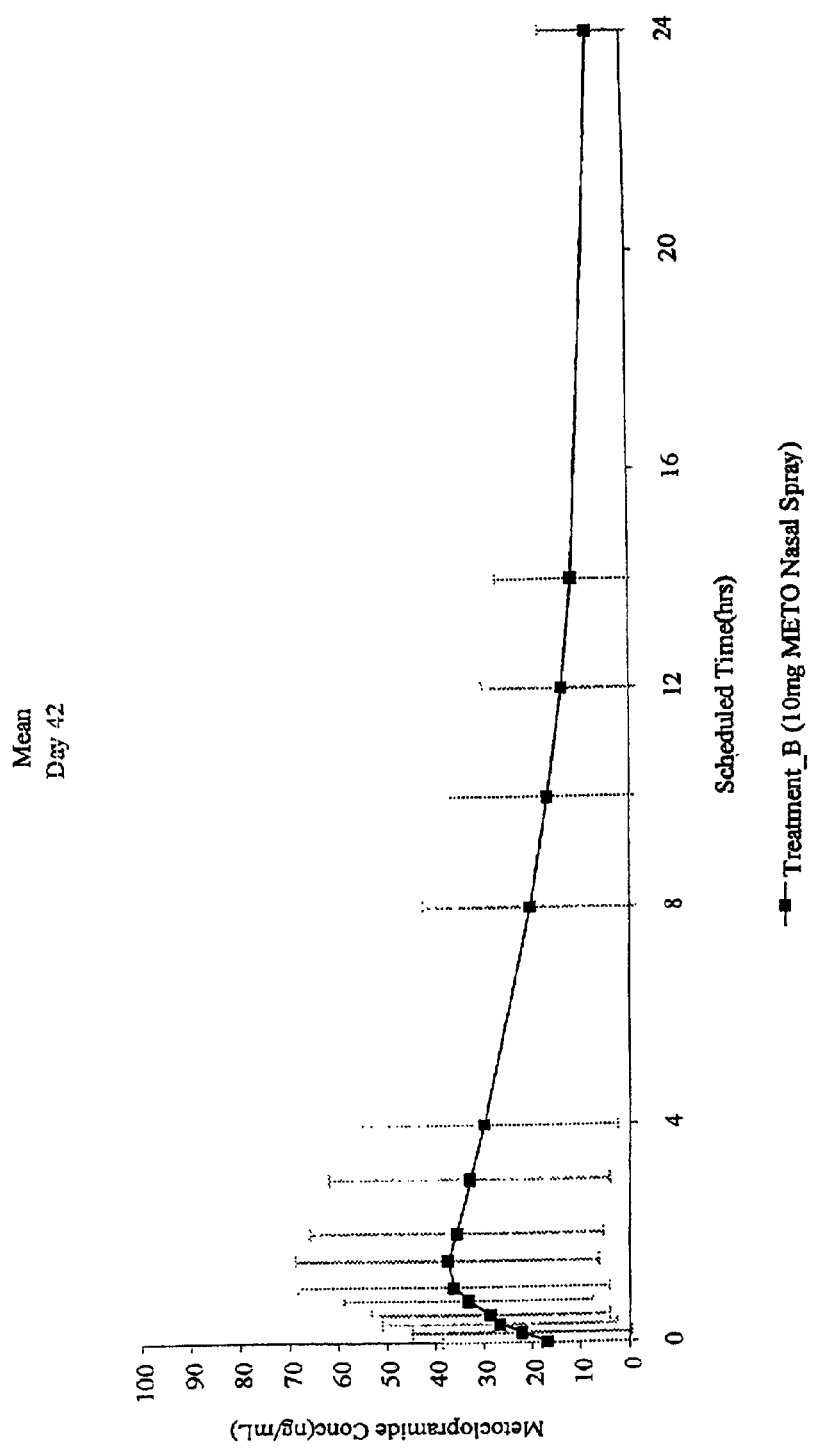
Figure 4C:
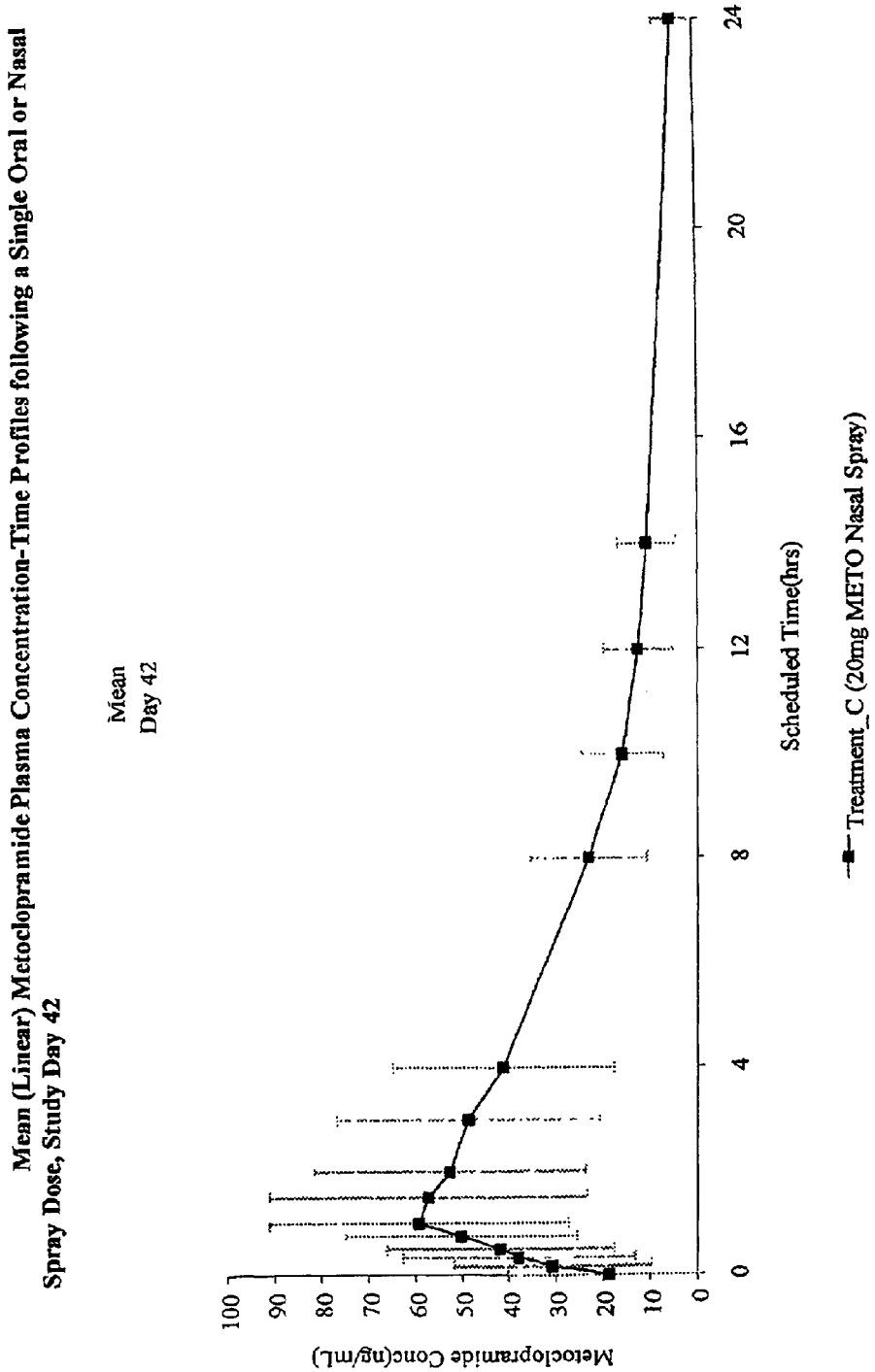

FIG. 1 is a bar graph of the adjusted mean change from baseline to the end of the study for individual symptom scores;

FIGS. 2A, 2B and 2C contain the mean (linear) of metoclopramide plasma concentration over hours 0 through four following a single oral or nasal spray dose of metoclopramide on the first day of study; FIG. 2A is a graph of 10 mg oral; FIG. 2B is 10 mg nasal; FIG. 2C is 20 mg nasal;

FIGS. 3A, 3B and 3C contain the mean (linear) of metoclopramide plasma concentration over hours 0 through twenty-four following a single oral or nasal spray dose of metoclopramide on the first day of study; FIG. 3A is a graph of 10 mg oral; FIG. 3B is 10 mg nasal; FIG. 3C is 20 mg nasal;

FIGS. 4A, 4B and 4C contain the mean (linear) of metoclopramide plasma concentration over hours 0 through twenty-four following a single oral or nasal spray dose of metoclopramide on the forty-second day of study; FIG. 4A is a graph of 10 mg oral; FIG. 4B is 10 mg nasal; FIG. 4C is 20 mg nasal.

5. DETAILED DESCRIPTION

The invention is directed to a method for treating and controlling gastroparesis by nasally administering MCP or a pharmaceutically acceptable salt thereof. MCP is formulated to contain a therapeutically effective amount of MCP such that upon administration by the intranasal route, a therapeutically effective amount of MCP is delivered to the patient. In addition, the therapeutically effective amount of MCP, in both aqueous and non-aqueous formulations, is chosen to minimize the severity and incidence of untoward side-effects and drug-interactions encountered with MCP. Compared to the injectable form and oral form of MCP, intranasal administration of MCP has the advantage of being painless, effective, safe, and consistent, particularly for patients with gastroparesis.

5.1 Pharmacokinetic Data: Selection of Doses in the Study

The pharmacokinetic data from three single dose, cross-over pharmacokinetic studies in healthy patients vas evaluated to determine appropriate dose selection for the clinical study described in sections 6 and 7.

In one study (data not shown), the relative bioavailability (nasal versus oral) was determined to be 52/57% in terms of $AUC_{0-inf}$ (area under the plasma concentration-time curve extrapolated to infinity) and 31/41% in terms of $C_{max}$ (maximum observed concentration). The absolute bioavailability (nasal versus IV) in terms of $AUC_{0-inf}$ was 42/45% (two different nasal spray concentrations were evaluated, 200 mg/ml and 400 mg/ml).

In a second study (data not shown), the relative bioavailability (nasal versus oral) was determined to be 97% in terms of $AUC_{0-inf}$ and 72% in terms of $C_{max}$. The absolute bioavailability (nasal versus IV) in terms of $AUC_{0-inf}$ was also 97%.

In a third study (data not shown), the absolute bioavailability of the nasal spray (nasal versus IV) was determined to be 69%.

Given the disparity in these studies, a pooled analysis of the data from the first and second study was performed. This resulted in a relative bioavailability of 58% (90% CI: 49%–68%) for $AUC_{0-inf}$ and 45% (90% CI: 36%–57%) for $C_{max}$.

It was therefore determined appropriate to study safety and efficacy of both 10 mg and 20 mg doses of nasal spray for the treatment of diabetic gastroparesis.

In one embodiment of the present invention, gastroparesis is treated by intranasally administering a pharmaceutically acceptable MCP nasal dosage form at a therapeutic dosage level of between about 20 mg/day to about 160 mg/day for about 1 to about 8 weeks. The duration of treatment is preferably about 5 weeks to about 8 weeks, and most preferably about 6 weeks.

In another embodiment of the invention, a method for treating gastroparesis is provided by intranasally administering a pharmaceutically acceptable MCP nasal dosage form at a therapeutic dosage level of between about 40 mg/day to about 160 mg/day in 3 to 4 smaller dosages at equally spaced intervals within 24 hours for about 1 to about 8 weeks. It is understood that the daily dosing is varied with the particular needs of the patients to be treated and that one of skill in the art is expected to modify dosing in a manner most suitable for a particular patient, i.e., one dose per day, two, three, four, five or any other regime most efficacious for the patient's needs. Thus, any suitable number of doses per day may be used. Further, all therapeutic dosage levels from about 20 mg/day to about 160 mg/day, are encompassed in the invention, including but not limited to, dosage levels of 30 mg/day, 35 mg/day, 40 mg/day, 45 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, and 160 mg/day. These daily dosages may be administered in smaller doses. Preferred smaller doses are 10 mg, 20 mg, and 30 mg. Preferred times for administration are 3–4 smaller dosages at equally spaced intervals within a 24-hour period or about 1–8 weeks. Alternative preferred times for administration are before meals, assuming 2 to 4 meals per day, and before bedtime. The duration of treatment is preferably about 5 weeks to about 8 weeks, and most preferably about 6 weeks.

In still another embodiment of the invention, a method for treating gastroparesis is provided by intranasally administering a pharmaceutically acceptable MCP nasal dosage form at a therapeutic dosage level of between about 40 mg/day to about 80 mg/day for about 1 to about 8 weeks. The duration of treatment is preferably about 5 weeks to about 8 weeks, and most preferably about 6 weeks.

In an additional embodiment of the invention, a method for treating gastroparesis is provided by intranasally administering a pharmaceutically acceptable MCP nasal dosage form at a therapeutic dosage level of about 80 mg/day in 3 to 4 smaller dosages at equally spaced intervals within 24 hours for about 1 to about 8 weeks. The duration of treatment is preferably about 5 weeks to about 8 weeks, and most preferably about 6 weeks.

In particular, the invention is directed to a method for treating gastroparesis caused by a number of origins, including but not limited to, diabetes (including type 1 and type 2), postviral syndromes, anorexia nervosa, surgery on the on the stomach or vagus nerve, medications, particularly anticholinergics and narcotics which slow contractions in the intestine, gastroesophageal reflux disease, smooth muscle disorders such as amyloidosis and scleroderma, nervous system diseases (including abdominal migraine and Parkinson's disease), or metabolic disorders (including hypothyroidism).

In a preferred embodiment, the gastroparesis is of diabetic origin, including type 1 and type 2 diabetes. Treatment generally involves intranasally administering a pharmaceutically acceptable MCP nasal spray dosage form at a therapeutic dosage level of between about 40 mg/day to about 160 mg/day in 3 to 4 smaller dosages at equally spaced intervals within 24 hours for about 1 to about 8 weeks, preferably for about 2 weeks to about 8 weeks, and most preferably for about 6 weeks.

In a preferred embodiment, treatment involves intranasally administering a pharmaceutically acceptable MCP nasal dosage form at a therapeutic dosage level of between about 40 mg/day to about 80 mg/day in 3 to 4 smaller dosages at equally spaced intervals within 24 hours for about 1 to about 8 weeks, preferably for about 5 weeks to about 8 weeks, and most preferably for about 6 weeks.

In one embodiment, the MCP nasal formulation administered to deliver a dose of 10 mg four times a day comprises:

| | |
|---|---|
| 10 mg/0.1 ml | metoclopramide hydrochloride |
| 1.5 mg | benzyl alcohol |
| 0.8 mg | NaCl |
| 0.320 mg | glacial acetic acid |
| 0.077 mg | sodium acetate |
| 6.425 mg | sorbitol |
| 0.8–1 mg/ml | menthol |
| 1 mg/ml | edetate disodium |
| 0.1 ml | purified water (qs ad to 0.1 ml) |

The MCP nasal formulation is given to patients as either 1 puff in one and only one nostril (i.e., 1 puff at 10 mg/puff (10 mg/0.1 ml and 0.1 ml/puff)) four times a day (1 puff QID for about 1, 2, 3, 4, 5, 6, 7, or 8 weeks), or 1 puff per nostril in both nostrils (i.e., 2 puffs at 5 mg/puff (10 mg/0.1 ml and 0.05 ml/puff)) four times a day (2 puffs QID for about 1, 2, 3, 4, 5, 6, 7, or 8 weeks). The above formulation is sterile with a bacteria count of 10 below the level allowed by the U.S. Patent on a per ml basis. In addition, pathogens are absent. The pH of the above formulation is about 4.0.

In other embodiment, the MCP nasal formulation administered to deliver a dose of 20 mg four times a day comprises (formulation per 0.1 ml of MCP nasal (MCP n=metoclopramide nasal dosage form)):

| | |
|---|---|
| 20 mg/0.1 ml | metoclopramide hydrochloride |
| 1.5 mg | benzyl alcohol |
| 0.8 mg | NaCl |
| 0.320 mg | glacial acetic acid |
| 0.077 mg | sodium acetate |
| 6.425 mg | sorbitol |
| 0.8–1 mg/ml | menthol |
| 1 mg/ml | edetate disodium |
| 0.1 ml | purified water (qs ad to 0.1 ml). |

The MCP nasal formulation is given to patients as either 1 puff in one and only one nostril (i.e., 1 puff at 20 mg/puff (20 mg/0.1 ml and 0.1 ml/puff)) four times a day (1 puff QID for about 1, 2, 3, 4, 5, 6, 7, or 8 weeks), or 1 puff per nostril in both nostrils (i.e., 2 puffs at 10 mg/puff (20 mg/0.1 ml and 0.05 ml/puff)) four times a day (2 puffs QID for about 1, 2, 3, 4, 5, 6, 7, or 8 weeks). The above formulation is sterile with a bacteria count of 10 below the level allowed by the U.S. Patent on a per ml basis. In addition, pathogens are absent. The pH of the above formulation is about 4.0.

In yet another embodiment, the MCP nasal formulation administered to deliver a dose of 30 mg four times a day comprises (formulation per 0.1 ml of MCP nasal spray (MCP n=metoclopramide nasal dosage form)):

| | |
|---|---|
| 30 mg/0.1 ml | metoclopramide hydrochloride |
| 1.5 mg | benzyl alcohol |
| 0.8 mg | NaCl |
| 0.320 mg | glacial acetic acid |
| 0.077 mg | sodium acetate |
| 6.425 mg | sorbitol |
| 0.8–1 mg/ml | menthol |
| 1 mg/ml | edetate disodium |
| 0.1 ml | purified water (qs ad to 0.1 ml) |

The MCP nasal formulation is given to patients as either 1 puff in one and only one nostril (i.e., 1 puff at 30 mg/puff (30 mg/0.1 ml and 0.1 ml/puff)) four times a day (1 puff QID for about 1, 2, 3, 4, 5, 6, 7, or 8 weeks), or 1 puff per nostril in both nostrils (i.e., 2 puffs at 15 mg/puff (20 mg/0.1 ml and 0.075 ml/puff)) four times a day (2 puffs QID for about 1, 2, 3, 4, 5, 6, 7, or 8 weeks). The above formulation is sterile with a bacteria count of 10 below the level allowed by the U.S. Patent on a per ml basis. In addition, pathogens are absent. The pH of the above formulation is about 4.0.

Additional formulations may be prepared to deliver other doses of metoclopramide for nasal administration and may be formulated as above, substituting the amount of metoclopramide per milliliter, i.e., a dose of 15 mg would be 15 mg/0.1 ml, a dose of 30 mg would be 30 mg/0.1 ml, etc.

Thus, it is expected that one of ordinary skill would be able to formulate nasal formulations having different concentrations of MCP such as, for example, formulations where 1 puff of 0.1 ml/puff would deliver 25 mg/puff, 35 mg/puff, 40 mg/puff, etc. Also, one of skill in the art is presumed to know the appropriate concentration of MCP/ puff depending on the desired administration i.e., 1 puff/ nostril for one nostril or, alternatively, both nostrils and is expected to adjust the concentrations of MCP accordingly.

Further, suitable nontoxic pharmaceutically acceptable nasal carriers for MCP will be apparent to those skilled in the art of nasal pharmaceutical formulations. Also see REMINGTON'S PHARMACEUTICAL SCIENCES, any edition. Obviously, the choice of suitable carriers will depend on the exact nature of the particular nasal dosage form required, e.g., whether the drug is to be formulated into a nasal solution (for use as drops or as a spray, can be either oil or aqueous-based), a nasal suspension, a nasal ointment, a nasal gel or another nasal form, all of which are encompassed by the present invention. Preferred nasal dosage forms are solutions, suspensions and gels. Minor amounts of ingredients such as pH adjusters (e.g., a base such as NaOH), emulsifiers or dispersing agents, buffering agents, preservatives such as agents which prevent degradation of MCP and in particular the oxidation of MCP, wetting agents, jelling agents (e.g., methylcellulose) and flavoring agents may also be present. Preferably about 1 mg/ml of edetate disodium (or another agent which prevents oxidation of metoclopramide) and about 0.08–1 mg/ml of menthol or menthol crystals is added.

Most preferably, the nasal composition is isotonic. If desired, sustained release nasal compositions, e.g., sustained release gels, or when a more highly insoluble form is desired, a long chain carboxylic acid salt of the drug can be conveniently employed. The carboxylic acid portion of the salt preferably contains 10 to 20 carbon atoms. Alternatively, equimolar amounts of the drug free base and the long chain carboxylic acid are combined in methanol. That mixture is then added to a small volume of water, causing the desired salt (e.g., drug stearate) to precipitate out. One of skill in the art is presumed to be aware of other suitable aqueous and non-aqueous embodiments for sustained release formulations.

Those skilled in the art will be aware that a systemic, therapeutically effective amount of MCP for treating gastroparesis will vary with the age, size, weight and general physical condition of the patient as well as the severity of the disease. Frequency of administration will likewise vary with the formulation of nasal metoclopramide (i.e., the concentration of MCP, whether it is in the form of sustained release, etc.) and can be adjusted so that any suitable number of doses per day may be used.

As a practical matter the selected therapeutic compositions will normally be prepared in dosage unit forms to contain systemic, therapeutically effective amounts of the selected MCP.

Typical MCP nasal dosage forms are solutions or suspensions that can be administered as a nasal spray. However, nasal drops may also be used. Nasal spray or nasal drops may comprise aqueous or non-aqueous solutions or suspensions of MCP. The MCP nasal spray dosage formulation contains the active agent in any suitable form and pharmaceutically acceptable salt thereof (e.g. metoclopramide hydrochloride).

A typical MCP nasal formulation is in solution form having a light amber color and being non-cloudy to the naked eye with an pH of between about 3.0–5.0. The typical formulation may contain benzyl alcohol of at least about 13.5 mg/ml containing practically no impurities as determined by high pressure liquid chromatography (HPLC) and having a bacterial count of less than 250 ufc/ml and free of pathogens sufficient to form an acceptable pharmaceutical nasal spray dosage form. The solvent may be purified water suitable for use in nasal dosage forms or any equivalent water (e.g. injectable water) that is allowed for use in such nasal dosage forms. See REMINGTON'S PHARMACEUTICAL SCIENCES, any edition from 1980–1996. For the adequate and/or sufficient treatment and control of gastroparesis, a typical dose is that dose which is therapeutically effective and which minimizes side-effects and drug interactions.

The formulations used in the methods of the invention also include one or more other drugs being co-administered with the nasal metoclopramide. These drugs can be administered concurrently with metoclopramide or at separate time intervals. Alternatively, one or more other drugs may be incorporated into the metoclopramide nasal formulation. These drugs include pain relievers, insulin and other drugs useful in the management of diabetes, steroids, especially steroids that prevent nasal irritation, and antidepressants. It is preferred that the co-administered drug be one that is not known to cause adverse side effects when administered with metoclopramide.

A typical nasal dosage of MCP for the treatment and control of gastroparesis depends upon the degree and severity of gastroparesis experienced by a typical patient (e.g. caused by diabetes). Some individuals with diabetic gastroparesis may experience symptom-free periods interspersed with intermittent acute exacerbations. Others may have chronic, ongoing symptoms that wax and wane over time. Disease severity falls along a wide continuum. Some diabetics may be completely asymptomatic despite measurable delays in gastric emptying. Others may have symptoms that affect their lifestyles or daily activities to varying degrees. Although rare, complete gastric atony can be a life-threatening complication of diabetic gastroparesis, requiring hospitalization and supportive measures of intravenous hydration or nutrition. All of the above states of gastroparesis disease are encompassed by the invention.

The dosage of the nasally administered MCP may be varied between about 20 mg/day to about 160 mg/day. Above about 160 mg/day, the dosage may be undesirable due to untoward side effects experienced by patients receiving more than about 160 mg/day from the MCP nasal dosage form. A preferred dosage of MCP nasal spray is 40 to 80 mg/day. Typically, administration of, for example, 80 mg/day is given as 20 mg four times a day (for example, either (1) 2 puffs of 10 mg/0.1 ml of MCP nasal spray, one puff per nostril, (2) 2 puffs of 10 mg/0.05 ml of MCP nasal spray, one puff per nostril, or (3) 1 puff of 20 mg/0.1 ml of MCP nasal spray in one and only one nostril).

Various techniques may be used to assess the severity of the gastroparesis and gastric emptying. Methods well known in this art include, for example, questioning the patient on symptoms related to the disease as well as techniques such as radioscintigraphy, ultrasonography, and techniques using radiopaque markers such as barium. Radioscintigraphy appears to be the preferred method, due to its relatively high sensitivity and specificity, ease of use, and low exposure to radiation. All of these methods can be used to determine, together with teachings of the present invention, the appropriate dosage for a particular patient.

The weight of the patient may also affect the dosage to be administered. Typically, a dose of between about 0.1 mg/kg to about 2.5 mg/kg is given to a patient suffering from gastroparesis. The dosages can be either about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg. A preferred nasal dosage is between about 0.06 to about 1.2 mg/kg of body weight. Other preferred nasal dosages are about 0.06 mg/kg, 0.08 mg/kg, 1.0 mg/kg, 1.2 mg/kg and 1.4 mg/kg.

The aforementioned dosages for the treatment and control of gastroparesis are usually given before meals and before bed time.

The expected benefit of an intranasal formulation of metoclopramide for gastroparesis is to provide an alternative route of administration for this agent to patients who have uncomfortable gastrointestinal symptoms of gastroparesis. The intranasal formulation of metoclopramide will spare patients with active symptoms the potential additional discomfort of having to swallow an oral formulation and serves as an alternative to injectable formulations. As presented in greater detail below in Section 6, the nasal administration of metoclopramide treatment of gastroparesis offers many benefits, some of which are unexpected. For example, as illustrated below, one unexpected benefit is that while patents receiving the nasal form of the drug were exposed to less drug overall, 10 mg of nasal metoclopramide was superior to 10 mg oral metoclopramide in reducing symptoms with particular significance in the categories of feeling full after eating and persistent fullness. Further, less exposure to metoclopramide reduces the opportunity for central nervous system (CNS) side effects (see the data relating to $AUC_{0-inf}$ for 10 mg oral versus nasal). Also, the benefit of the 20 mg nasal (80 mg/day) was superior than 10 mg oral in for all symptoms studied and was well tolerated for six weeks. In contrast, 80 mg/day of oral metoclopramide would be expected to result in significant CNS side effects and is not indicated for such duration. However, nasal doses of 80 mg/day were well tolerated for an extended period of six weeks. Further, because of its rapid onset of action (see FIGS. 2B and 2C showing higher initial blood levels, i.e., faster absorption), nasal metoclopramide may be substituted for intravenous administration in patients with severe gastroparesis for whom the oral form is not indicated. The benefits of nasal administration over intravenous administration being obvious to the skilled practitioner. In sum, the nasal form of metoclopramide, as demonstrated herein, provides heretofore unexpected benefits in the treatment of gastroparesis.

Various publications are cited herein, the disclosures of which are incorporated by reference in their entirety for all purposes.

Having described the invention, the following examples are included to illustrate the benefits of the present invention. The examples are only illustrative and are not meant to unduly limit the scope of the present invention.

6. EXAMPLES

6.1 Overall Study Design and Plan

A multi-center, controlled, randomized, open-label, parallel design study in patients with diabetic gastroparesis was done. Eligible patients were randomized to receive metoclopramide nasal spray 10 mg, metoclopramide nasal spray 20 mg or oral metoclopramide 10 mg tablets in ratio 2:2:1 four times daily before meals and at bedtime for six weeks.

6.2 Treatments Administered

Intranasal Medication: The metoclopramide 200 mg/ml solution was packaged with a Valois VP7-50 pump which delivers 0.05 ml per spray for the 10 mg strength, and with a Valois VP7-100 pump which delivers 0.1 ml per spray for the 20 mg strength. Patients randomized to receive metoclopramide nasal spray 10 mg or 20 mg received one spray per dose. The formulation was as follows:

| | |
|---|---|
| 20 mg/0.1 ml | metoclopramide hydrochloride |
| 1.5 mg | benzyl alcohol |
| 0.8 mg | NaCl |
| 0.320 mg | glacial acetic acid |
| 0.077 mg | sodium acetate |
| 6.425 mg | sorbitol |
| 0.8–1 mg/ml | menthol |
| 1 mg/ml | edetate disodium |
| 0.1 ml | purified water (qs ad to 0.1 ml). |

6.3 Randomized Treatment or Crossover Phase

Patients who were determined eligible for inclusion in the study following the screening visit were block-randomized within each center in a 2:2:1 ratio (metoclopramide nasal spray 10 mg, metoclopramide nasal spray 20 mg and oral metoclopramide 10 mg respectively) with a block size of 5.

6.4 Method of Assigning Patients to Treatment Groups

Patients were randomly assigned to receive their allocated treatment according to a computer-generated randomization schedule prepared prior to the start of the study. Study patients who were deemed eligible for the protocol following the screening visit were randomized in a 2:2:1 fashion in blocks of 5, randomized within study center to receive metoclopramide nasal spray 10 mg or 20 mg or oral metoclopramide 10 mg tablets, respectively.

6.5 Selection and Timing of Dose for Each Patient

All patients randomized to nasal spray were instructed to do the following: actuate the nasal spray device once into one nostril, four times daily, before meals and at bedtime; alternate nostrils with each application.

Patients randomized to oral metoclopramide tablets were instructed to take one tablet four times daily, 30 minutes before meals and at bedtime.

If the patient skipped a meal, he/she was instructed to still take medication as scheduled. If the patient ate more than three meals in one day, he/she was instructed to not take additional medication. If a dose of medication was forgotten, he/she was advised to take it as soon as he/she remembered. Doses greater than 2 hours late were omitted. The patients were instructed not to take a double dose of the medication at the next scheduled time if a dose was missed.

There were no dose adjustments allowed during the conduct of the study.

Patients began taking the medication on study Day 1 and completed on Day 42.

6.6 Symptom Assessment

A symptom assessment tool, modified from the tool described by Perkel and colleagues (M. S. Perkel, T. Hersh, C. Moore, E. D. Davidson, "Metoclopramide Therapy in Fifty-five Patients With Delayed Gastric Emptying"; Am J Gastroenterol 1980; 74:231–236) which is incorporated herein in its entirety, was used to assess symptoms and therapeutic efficacy before, during, and at the conclusion of treatment. The modifications to the Perkel scale included removal of items which were redundant or are not considered hallmark symptoms of gastroparesis. Simple language changes (medical to layman terminology) and more precise response specifications were also included to increase inter-site consistency and were self-reported on the Symptom Assessment Questionnaire ("SAQ"). Patients were asked to rate the frequency of each of six target symptoms during the week prior to the assessment. The target symptoms were nausea, vomiting, anorexia, bloating, early satiety and meal tolerance. Patients assigned each symptom a predefined ordinal frequency score of zero to four.

Also included was an assessment of severity in the evaluation of diabetic gastroparesis symptoms (W. S. Longo, A. M. Vernava; "Prokinetic Agents for Lower Gastrointestinal Motility Disorders", Dis Colon Rectum 1993; 36:696–708) and is incorporated by reference in its entirety. An Investigator's Assessment Questionnaire ("IAQ") was included to assess the severity of the symptoms and therapeutic efficacy before, during, and at the conclusion of treatment following speaking to the patient.

A total symptom score was calculated as the sum of the ratings of the SAQ and IAQ.

Entry criteria for the study included a total score of between 8 and 20 on each of the SAQ and IAQ, based upon a moderate or greater grading of at least two symptoms and varying grading on other symptoms. Patients with a score higher than 40 were excluded. On each of the scales (SAQ and IAQ), a minimum of two out of six symptoms must have been rated moderate (2) or higher.

6.7 Efficacy Parameters

Efficacy measurements included the patient's SAQ and IAQ scores. Both questionnaires were completed at baseline and once per week during the 6 week treatment period: Days 7, 14, 21, 28, 35 and 42, respectively.

The SAQ and IAQ each had 6 symptom items, including nausea, vomiting, loss of appetite, feeling bloated, feeling full after eating a small amount of food, and persistent fullness after eating. The SAQ assessed the frequency of the symptoms, whereas the IAQ examined the severity. The SAQ was completed first since the physician needed to discuss the symptoms with the patient prior to the completion of the IAQ.

6.8 Primary Efficacy Parameter

The primary efficacy endpoint was the change from the baseline to the end of the study in the total symptom score. The total symptom score is the sum of the six patient-rated frequency items plus the sum of the six investigator-rated severity items. If a patient terminated prematurely from the study, the last available total symptom assessment score was used.

6.9 Secondary Efficacy Parameter

The secondary efficacy endpoints involved both changes from baseline in the weekly total symptom scores and combined severity and frequency score (severity score plus frequency score) for each individual symptom. Each combined item has a possible score of 0 to 8.

7. RESULTS 7.1 Efficacy Analysis

The primary efficacy endpoint for the study was the change in total symptom score between baseline and week 6. The primary analysis of efficacy was an intent-to-treat analysis where all patients who were randomized to one of the three treatments and had at least one post-randomization assessment (including SAQ and IAQ) were included. Of the 89 patients who were randomized, two patients (04/002 and 05/919) were excluded because there were no data to assess efficacy collected after they are randomized.

The secondary analysis of efficacy was a "per protocol" analysis which included all patients who completed the study per protocol. This per protocol analysis was performed only for the primary efficacy endpoint, i.e., the change from baseline to the end of the study in the total symptom score. Patients who did not meet the baseline SAQ/IAQ score criteria were excluded. The SAQ and IAQ taken during the time interval in which prohibited concomitant therapies were taken was also excluded from the per protocol analysis. The statistical analysis results for the Individual Symptom Score analysis and for the per protocol analysis are provided in Table 1 and Table 2, respectively.

TABLE 1

Adjusted Mean Change From Baseline To The End of Study For Total Symptom Score (ITT)
PROTOCOL: Emitasol Nasal Spray
Adjusted Mean Change from Baseline to the End of Study for Total Symptom Score
(Intent-to-Treat)

| Treatment | N | Baseline Mean | Mean Change* From Baseline | Difference From Oral 10 mg Mean (95% C.I.) | P-value |
|---|---|---|---|---|---|
| Oral 10 mg | 18 | 22.9 | −14.3 | | |
| Nasal 10 mg | 34 | 23.4 | −16.8 | −2.5 (−5.8, 0.8) | 0.132 |
| Nasal 20 mg | 35 | 21.3 | −18.0 | −3.8 (−7.1, −0.5) | 0.026 |

*Baseline total symptom score and study center adjusted mean change

TABLE 2

Adjusted Mean Change From Baseline To The End of Study For Individual Symptom Score (Per Protocol)
PROTOCOL: Emitasol Nasal Spray
Adjusted Mean Change from Baseline to the End of Study for Total Symptom Score
(Per-Protocol)

| Treatment | N | Baseline Mean | Mean Change* From Baseline | Difference From Oral 10 mg Mean (95% C.I.) | P-value |
|---|---|---|---|---|---|
| Oral 10 mg | 16 | 22.8 | −13.9 | | |
| Nasal 10 mg | 30 | 23.4 | −17.7 | −3.8 (−7.1, −0.5) | 0.026 |
| Nasal 20 mg | 30 | 21.3 | −18.4 | −4.6 (−7.9, −1.2) | 0.008 |

*Baseline total symptom score and study center adjusted mean change

There was a statistically significant difference between the change from baseline in the total symptom score between the nasal 20 mg and oral 10 mg cohorts at week 6 (p=0.026). In addition, both the nasal 10 mg and the nasal 20 mg groups had better mean total symptom scores compared to the oral 10 mg group, i.e., compared to the oral 10 mg group the score was 2.5 points better for nasal 10 mg and 3.8 points better for nasal 20 mg.

After the exclusion of protocol violators, similar results were observed in the per protocol analysis. In the per protocol analyses there was a significant difference in the total symptom score between baseline and week 6 for both the nasal 10 mg (p=0.026) and nasal 20 mg (p=0.008) cohorts compared to the oral 10 mg group.

7.1.2 Secondary Efficacy Parameters

Total Symptom Score Profile and Symptom Item Scores

Table 3 summarizes the change overtime in total symptom scores for patients enrolled into the clinical study.

TABLE 3

Adjusted Mean Change From Baseline To The End of
Study For Total Symptom Score by Treatment (ITT)
PROTOCOL: Emitasol Nasal Spray
Summary of Mean Change from Baseline to the End of Study for
Total Symptom Score by Treatment
(Intent-to-Treat)

| Treatment | N | Baseline Mean | End of Study Mean (SD) | Change From Baseline Mean (SD) |
|---|---|---|---|---|
| Oral 10 mg | 18 | 22.9 (6.1) | 7.6 (7.0) | −15.3 (8.7) |
| Nasal 10 mg | 34 | 23.4 (6.5) | 5.3 (7.0) | −18.1 (8.9) |
| Nasal 20 mg | 35 | 21.3 (4.9) | 3.8 (4.3) | −17.6 (4.9) |

For all three metoclopramide groups, the mean total symptom scores reduced more than 13 points from baseline after one week of treatment with both nasal treatments scoring above the oral. A treatment effect was seen for all 6 items scored, i.e., there was a reduction in the scores for each of the symptoms: nausea, vomiting, loss of appetite, feeling bloated, feeling full after eating a small amount of food, and persistent fullness after eating.

Table 4 provides the analysis results for each of the 6 symptom items. There was a statistically significant difference for 3 symptoms in the change in score from baseline and week 6 between the nasal 20 mg and oral 10 mg groups: loss of appetite (p=0.019), feeling full after eating a small amount of food (p=0.010), and persistent fullness after eating (p=0.003). There was a statistically significant difference between the nasal 10 mg and oral 10 mg groups for one symptom, feeling full after eating a small amount of food (p=0.021). All test p-values in Table 4 are presented without adjustment for multiplicity.

TABLE 4

Adjusted Mean Change From Baseline To The End of Study
For Individual Symptom Score (ITT)
PROTOCOL: Emitasol Nasal Spray
Adjusted Mean Change from Baseline to the End of Study
for Individual Symptom Score
(Intent-to-Treat)

| Symptom | Treatment | N | Baseline Mean | Mean Change* From Baseline | Difference From Oral 10 mg Mean (95% C.I.) | P-value |
|---|---|---|---|---|---|---|
| Nausea | Oral 10 mg | 18 | 3.9 | −2.5 | | |
| | Nasal 10 mg | 34 | 3.7 | −2.7 | −0.2 (−1.0, 0.5) | 0.564 |
| | Nasal 20 mg | 35 | 2.9 | −2.8 | −0.3 (−1.1, 0.5) | 0.423 |
| Vomiting | Oral 10 mg | 18 | 1.6 | −0.9 | | |
| | Nasal 10 mg | 34 | 1.1 | −0.8 | 0.1 (−0.4, 0.5) | 0.757 |
| | Nasal 20 mg | 35 | 0.8 | −1.1 | −0.2 (−0.6, 0.3) | 0.435 |
| Loss of Appetite | Oral 10 mg | 18 | 3.8 | −2.3 | | |
| | Nasal 10 mg | 34 | 3.9 | −2.8 | −0.5 (−1.2, 0.2) | 0.174 |
| | Nasal 20 mg | 35 | 3.2 | −3.1 | −0.9 (−1.6, −0.1) | 0.109 |
| Feeling Bloated | Oral 10 mg | 18 | 4.8 | −3.1 | | |
| | Nasal 10 mg | 34 | 4.9 | −3.3 | −0.2 (−1.2, 0.8) | 0.707 |
| | Nasal 20 mg | 35 | 4.7 | −3.4 | −0.3 (−1.3, 0.7) | 0.549 |
| Feeling Full After Eating | Oral 10 mg | 18 | 4.3 | −2.5 | | |
| | Nasal 10 mg | 34 | 5.0 | −3.5 | −1.0 (−1.8, −0.1) | 0.021 |
| | Nasal 20 mg | 35 | 4.8 | −3.6 | −1.1 (−1.9, −0.3) | 0.010 |
| Persistent Fullness | Oral 10 mg | 18 | 4.5 | −2.9 | | |
| | Nasal 10 mg | 34 | 4.8 | −3.6 | −0.7 (−1.4, 0.0) | 0.061 |
| | Nasal 20 mg | 35 | 4.9 | −4.1 | −1.1 (−1.8, −0.4) | 0.003 |

*Baseline total symptom score and study center adjusted mean change

At the primary time point of week 6, metoclopramide nasal spray 20 mg was statistically significantly superior to metoclopramide oral 10 mg tablets with respect to mean change from baseline in total symptom scores. The results were consistent from analyses based on both intent-to-treat approach and per protocol approach.

Numerically, both metoclopramide nasal spray 10 mg and 20 mg showed better response over metoclopramide oral 10 mg in total symptom scores after 6 weeks of treatment. Compared to the oral 10 mg treatment in terms of change from baseline scores, a statistically significant difference was observed for nasal 20 mg on 3 items: loss of appetite, feeling full after eating a small amount of food, and persistent fullness after eating. A statistically significant difference was observed for nasal 10 mg on feeling full after eating a small amount of food.

8. SAFETY AND PHARMACOKINETIC EVALUATION

8.1 Extent of Exposure

The analysis of safety includes all patients who were randomized and received at least one dose of study drug. There were 89 patients enrolled into the clinical study. Eight-two (82) patients completed the study. Seven patients failed to complete the study.

Of the 82 patients who completed the clinical study, 79 (96.3%) received all doses of metoclopramide. Table 5 shows the extent of drug exposure on a biweekly basis for the three treatments.

Overall, approximately 63% (56/89) patients reported at least one adverse event. Other than nasal irritation and soreness, adverse events included the following: asthenia, flu syndrome, headache, infection, pain, bloating, constipation, diarrhea, nausea, vomiting, leukopenia, hypoglycemia, dizziness, somnolence, bronchitis, epistaxis, rhinorrhea, sinus pain and taste perversion. There was no statistically significant difference among treatment groups in terms of overall adverse events, although nasal irritation (generally mild) was reported by a significantly higher proportion of patients in the nasal groups (both 10 mg and 20 mg nasal groups).

TABLE 5

Number Of Patients Who Received
Study Through Different Timepoints

| | Oral - 10 mg | Nasal - 10 mg | Nasal - 20 mg |
|---|---|---|---|
| Enrolled | 18 | 35 | 36 |
| Duration of treatment | | | |
| At least 1 day | 18 (100%) | 35 (100%) | 36 (100%) |
| At least 14 days | 17 (94.4%) | 33 (94.3%) | 34 (94.4%) |
| At least 28 days | 17 (94.4%) | 33 (94.3%) | 34 (94.4%) |
| At least 42 days | 16 (88.9%) | 31 (88.6%) | 32 (88.9%) |

8.2 Plasma Pharmacokinetic Analysis of Metoclopramide on Study Day 1

Mean (linear) plots plasma concentration-time profiles of metoclopramide following a single oral 10 mg dose, a single nasal dose of 10 mg and a single nasal dose of 20 mg are presented in FIG. 3 (A, B, and C), respectively. Mean and median plots (data for median plots not shown) indicated that the plasma concentrations after a 10 mg nasal spray dose were lower compared with the 10 mg oral dose. The mean plot indicated that the concentrations were higher following a 20 mg nasal spray in comparison the 10 mg oral dose. The median plot showed more comparable concentration-time profiles for the 10 mg oral dose and 20 mg nasal spray treatment groups.

The absorption of metoclopramide appeared to be rapid, with comparable rates of absorption for all three treatment groups, but with a small lag-time of approximately 20 minutes for the tablet in comparison to both the 10 and 20 mg nasal sprays. This absorption lag can be seen in the mean (linear) 0–4 h plasma concentration-time profiles presented in FIG. 2 (A, B, and C). The lag-time difference between the oral and the nasal formulations following a single dose may be due to the dissolution time of the tablet, or a combined effect of dissolution of the tablet and a rapid initial absorption of the nasal spray from the nasal mucosa. The elimination of the drug appeared to be monophasic in all three treatment groups.

The mean maximum concentration $C_{max}$ was higher following administration of the 20 mg nasal spray in comparison to the 10 mg tablet formulation with mean values of 48.68 (range: 12.10–107.00) and 36.41 (range: 12.5–61.10) ng/mL, respectively. The mean maximum concentration of the 10 mg nasal spray was lower and more variable with a mean maximum concentration of 29.13 (range: 2.21–103.00) ng/mL.

The area under the plasma concentration-time curve up to the last quantifiable concentration, $AUC_{0-t}$, was greatest following administration of the 20 mg nasal spray in comparison to the 10 mg tablet formulation, with mean values of 359.10 (range: 83.30–883.97) and 265.52 (range: 92.32–633.94). The mean $AUC_{0-inf}$ for the 10 mg nasal spray was lower than the 10 mg tablet formulation with a mean exposure of 221.44 (range: 31.13–800.97) ng.h/mL.

In terms of total exposure, $AUC_{0-inf}$ was greatest following administration of the 20 mg nasal spray in comparison to the 10 mg tablet formulation, with mean values of 412.12 (range: 105.57–1282.91) and 304.09 (range: 104.54–783.61) ng.h/mL. The mean $AUC_{0-inf}$ for the 10 mg nasal spray was the lowest, with a value of 268.97 (range: 43.09–1056.29) ng.h/mL. For the majority of patients, the mean percentage of $AUC_{0-inf}$ ex was less than 20%, but was larger for some patients in the nasal spray groups with a percentage extrapolated of up to 40.15%.

The mean terminal half-lives were 6.89 h, 6.90 h and 7.63 h for the 10 mg oral, 10 mg nasal and 20 mg nasal spray treatment groups, respectively. The median time to reach $C_{max}$, $T_{max}$ (time at which the maximum concentration was observed), was 1.5 h for all three treatment groups.

8.3 Plasma Pharmacokinetic Analysis of Metoclopramide on Study Day 42

The mean (linear) plots plasma concentration-time profiles of metoclopramide following repeated QID dosing on Days 2 through 42 and a single dose on Day 42 for the 10 mg oral, 10 mg nasal and 20 mg nasal treatments are presented in FIG. 4 (A, B, and C), respectively. Mean and median plots (data not shown) indicate that the plasma concentrations following a 10 mg nasal spray dose on Day 42 are lower when compared with those following the 10 mg oral dose. The mean and median plots showed similar concentrations after a 10 mg oral dose and 20 mg nasal spray dose.

Following multiple dosing there are minimal differences in systemic concentrations due to differences in dissolution and/or absorption routes. The elimination of the drug appeared to be monophasic in the three treatment groups.

The mean maximum concentrations on Day 42 were comparable between the 20 mg nasal and 10 mg oral treatment groups, with mean values of 67.23 (range: 2.96–152.00) and 61.21 (range: 22.60–106.00) ng/mL, respectively. The mean $C_{max}$ value for the 10 mg nasal treatment group was 41.11 (range: 11.10–146.00) ng/mL, approximately 67% of the mean value observed for the 10 mg oral treatment group, but with much higher variability.

In terms of exposure, the mean $AUC_{0-t}$ for the 20 mg nasal and the 10 mg oral treatment groups were comparable with mean values of 483.44 (range: 21.22–1094.63) and 481.11 (range: 119.46–988.34) ng.h/mL. The mean $AUC_{0-t}$ for the 10 mg nasal treatment group was 411.05 (range: 75.76–2198.68) ng.h/mL, approximately 85% of the mean exposure measured in the 10 mg tablet treatment group. This variability between patients was observed in all three treatment groups.

For the majority of patients, the mean percentage of $AUC_{0-inf}$ ex was less than 20%, but in some patients the percentage extrapolated was up to 37%.

The mean terminal half-livers were 8.44 h, 8.86 h and 8.03 h for the 10 mg oral, 10 mg nasal and 20 mg nasal treatment groups, respectively.

The median time to reach the maximum concentration $C_{max}$, $T_{max}$, was 1.00 h for the 10 mg oral and 20 mg nasal, and 1.50 h for the 10 mg nasal treatment group.

8.4 Accumulation

The area under the plasma concentration-time curve over the theoretical average dosing interval (tau), $AUC_{tau}$ (area under the plasma concentration-time curve over the theoretical average dosing interval tau) ($AUC_{0-6}$), where tau=6 h are as follows:

On Day 1, the mean $AUC_{tau}$ values were greatest following the 20 mg nasal spray treatment in comparison with the 10 mg nasal spray treatment, with mean values of 196.41 ng.h/mL and 138.37 ng.h/mL, respectively. In contrast, the $AUC_{tau}$ for the 10 mg nasal spray treatment was lower in comparison to the 10 mg oral treatment group, with a mean value of 113.39 ng.h/mL.

On Day 42, the mean values of $AUC_{tau}$ in patients administered multiple dosing of the 20 mg nasal spray treatment were approximately 10% higher than the $AUC_{tau}$ values in patients following multiple dosing with the 10 mg oral treatment. In contrast, the $AUC_{tau}$ in patients administered multiple dosing with the 10 mg nasal spray treatment were approximately 25% lower than the $AUC_{tau}$ inpatients in the 10 mg oral treatment groups.

The mean observed accumulation, determined as the ratio of the $AUC_{0-t}$ on day 42 to the $AUC_{0-t}$ on day 1, for a given treatment group were 1.95 (range: 0.96–4.47), 2.55 (range: 0.29–19.04) and 1.89 (range: 0.07–6.35), for the 10 mg oral, 10 mg nasal spray and the 20 mg nasal spray, respectively. These ratios indicate that at steady-state, the average plasma concentration of metoclopramide is approximately twice that following a single dose administration.

What is claimed is:

1. A method for treating or reducing the symptoms of gastroparesis in a patient comprising:
    administering metoclopramide or a pharmaceutically acceptable salt thereof to a patient in need of gastroparesis treatment, wherein said metoclopramide is in a pharmaceutically acceptable nasal spray formulation and administered intranasally in a therapeutically effective amount at a daily dosage of about 40 mg/day to about 160 mg/day for about 2 weeks to about 8 weeks, so that one or more symptoms of gastroparesis is treated or reduced.

2. The method of claim 1 wherein said daily dosage is administered for about 5 weeks to about 8 weeks.

3. The method of claim 1 wherein said daily dosage is administered for about 6 weeks.

4. The method of claim 1 wherein said daily dosage is between about 40 mg/day and about 80 mg/day.

5. The method of claim 1 wherein said daily dosage is about 40 mg/day.

6. The method of claim 1 wherein said daily dosage is about 80 mg/day.

7. The method of claim 1 wherein said daily dosage is between about 2.5 mg/kg and about 2.5 mg/kg.

8. The method of claim 7, wherein said daily dosage is between about 0.6 mg/kg and about 1.2 mg/kg.

9. A method for treating or reducing the symptoms of gastroparesis in a patient comprising:

administering metoclopramide or a pharmaceutically acceptable salt thereof to a patient in need of gastroparesis treatment, wherein said metoclopramide is in a pharmaceutically acceptable nasal formulation and administered intranasally as a spray or drops in a therapeutically effective amount at a daily dosage of between about 40 mg/day and about 160 mg/day, so that one or more symptoms of gastroparesis is treated or reduced.

10. The method of claim 9 wherein said deity dosage is between about 40 mg/day and about 80 mg/day.

11. The method of claim 9 wherein said daily dosage is about 40 mg/day.

12. The method of claim 9 wherein said daily dosage is about 80 mg/day.

13. The method of claim 9 wherein said daily dosage is between about 0.1 mg/kg and about 2.5 mg/kg.

14. The method of claim 13, wherein said daily dosage is between about 0.6 mg/kg and about 1.2 mg/kg.

15. The method of claim 1 or 9 wherein said daily dosage is divided into 3 or 4 equal doses and administered at equally spaced intervals within 24 hours.

16. The method of claim 15 wherein the doses are about 10 mg each.

17. The method of claim 15 wherein the doses are about 20 mg each.

18. The method of claim 1 or 9 wherein said daily dosage is divided into 3 or 4 equal doses and administered before meals.

19. The method of claim 18 wherein said doses are administered before meals and before bedtime.

20. The method of claim 18 wherein the doses are about 10 mg each when 4 doses are administered.

21. The method of claim 18 wherein the doses are about 20 mg each.

22. The method of claim 1 or 9 wherein the metoclopramide or pharmaceutically acceptable salt thereof is in an aqueous-based carrier.

23. The method of claim 1 or 9 wherein the metoclopramide or pharmaceutically acceptable salt thereof is in a sustained release formulation.

24. The method of claim 1 or 9 wherein the metoclopramide or pharmaceutically acceptable salt thereof is co-administered with one or more additional drugs.

25. The method of claim 1 or 9 wherein said dosage is administered for treating gastroparesis caused by any of: diabetes, a postviral syndrome, anorexia nervosa, surgery on the stomach or magus nerve, a medication, gastroesophageal reflux disease, smooth muscle disorder, a nervous system disease, or a metabolic disorder.

26. The method of claim 25 wherein said dosage is administered for treating gastroparesis caused by diabetes.

27. The method of claim 26 wherein said diabetes is selected from the group consisting of type 1 diabetes and type 2 diabetes.

28. The method of claim 25 wherein amid medication is selected from the group consisting of: anticholinergics, and narcotics which slow contractions in the intestine.

29. The method of claim 25 wherein said smooth muscle disorder is selected from the group consisting of: amyloidosis and scleroderma.

30. The method of claim 25 wherein said nervous system disease is selected from the group consisting of: abdominal migraine and Parkinson's disease.

31. The method of claim 25 wherein said metabolic disorder is hypothyroidism.

32. The method of claim 18 wherein said daily dosage is administered for about 2 to 6 weeks.

33. The method of claim 19 wherein said daily dosage is administered for about 2 to 6 weeks.

34. The method of claim 20 wherein said daily dosage is administered for about 2 to 6 weeks.

35. The method of claim 21 wherein said daily dosage is administered for about 2 to 6 weeks.

* * * * *

UNITED STATES PATENT AND TRADEMARK OFFICE
CERTIFICATE OF CORRECTION

PATENT NO. : 6,770,262 B2
DATED : August 27, 2004
INVENTOR(S) : Laura S. Lehman et al.

It is certified that error appears in the above-identified patent and that said Letters Patent is hereby corrected as shown below:

Column 17,
Line 8, please replace "between about 2.5 mg/kg and about 2.5 mg/kg." with
-- between about 0.1 mg/kg and about 2.5 mg/kg. --
Line 22, please replace "deity" with -- daily --

Column 18,
Line 16, please replace "magus" with -- vagus --
Line 24, please replace "amid" with -- said --

Signed and Sealed this

Seventh Day of December, 2004

JON W. DUDAS
*Director of the United States Patent and Trademark Office*